United States Patent [19]

Chappelle et al.

[11] Patent Number: 5,412,219
[45] Date of Patent: May 2, 1995

[54] METHOD FOR DETERMINING SURFACE COVERAGE BY MATERIALS EXHIBITING DIFFERENT FLUORESCENT PROPERTIES

[75] Inventors: Emmett W. Chappelle, Baltimore; Craig S. T. Daughtry, Columbia; James E. McMurtrey, III, Upper Marlboro, all of Md.

[73] Assignee: The United States of America as represented by the Administrator of the National Aeronautics and Space Administration, Washington, D.C.

[21] Appl. No.: 155,605

[22] Filed: Nov. 22, 1993

[51] Int. Cl.⁶ ............................................. G01N 21/64
[52] U.S. Cl. .................................. 250/461.1; 250/253
[58] Field of Search .............................. 250/461.1, 253

[56] References Cited

U.S. PATENT DOCUMENTS

| | | | |
|---|---|---|---|
| 3,043,908 | 7/1962 | Madsen | 348/144 |
| 4,087,685 | 5/1978 | Froot | 250/302 |
| 4,449,047 | 5/1984 | Monroe | 250/253 |
| 4,945,249 | 7/1990 | Grant et al. | 250/461.1 |

OTHER PUBLICATIONS

William R. Hemphill, Arnold F. Theisen, and R. Michael Tyson, "Laboratory Analysis and Airborne Detection of Materials Stimulated to Luminesce by the Sun" *Journal of Luminescence*, vols. 31 & 32, Part II (Dec. 1984) pp. 724–726 Copyright © Elsevier Science Publishers B.V.
Chappelle, McMurtrey, Daughtry, "A Fluorescence Technique for the Assessment of Crop Residue", Apr. 20, 1993, pp. 94–96. Place of publication not supplied by applicant.
McMurtrey, Chappelle, Daughtry, Kim, "Fluorescence and Reflectance of Crop Residue and Soil", May 1993 Journal of Soil and Water Conservation vol. 48, No. 3.
Daughtry, McMurtrey, Chappelle, Dulaney, Irons, Satterwhite, "Discriminating Crop Residues from Soil by Reflectance and Fluorescence Techniques", Aug. 1993 pp. 1325–1328 Place of publication not supplied by applicant.

*Primary Examiner*—Constantine Hannaher
*Attorney, Agent, or Firm*—Samual J. Petuchowski; R. Dennis Marchant; Guy M. Miller

[57] ABSTRACT

An improved method for detecting, measuring, and distinguishing crop residue, live vegetation, and mineral soil. By measuring fluorescence in multiple bands, live and dead vegetation are distinguished. The surface of the ground is illuminated with ultraviolet radiation, inducing fluorescence in certain molecules. The emitted fluorescent emission induced by the ultraviolet radiation is measured by means of a fluorescence detector, consisting of a photodetector or video camera and filters. The spectral content of the emitted fluorescent emission is characterized at each point sampled, and the proportion of the sampled area covered by residue or vegetation is calculated.

6 Claims, 4 Drawing Sheets

METHOD FOR DETERMINING SURFACE COVERAGE BY MATERIALS EXHIBITING DIFFERENT FLUORESCENT PROPERTIES

ORIGIN OF THE INVENTION

The invention described herein was made by employees of the United States Government, and may be manufactured and used by or for the Government for governmental purposes without the payment of any royalty thereon or therefor.

TECHNICAL FIELD

The present invention relates to luminophor irradiation by an ultraviolet source of radiation and more particularly to the discrimination and quantification of crop residue, live vegetation, and soil by irradiation thereof with an ultraviolet source.

BACKGROUND ART

Soil erosion from cropland is affected by the areal fraction of the land surface covered by crop residue, the non-living portion of a crop left in the field after harvest. Management of crop residues requires leaving a substantial amount of such residues in place in order to minimize soil erosion. As little as 30% coverage of the soil by residue can reduce soil erosion by approximately 90%. Proper crop residue management constitutes an important soil and water conservation measure and federal law requires the Chief of the Soil Conservation Service to maintain technical standards and criteria to assure that practices employed meet intended purposes. In order to manage such residues intelligently, a rapid, accurate, and objective measurement of the amount of crop residue cover on agricultural land is needed.

Two basic methods are currently employed for measuring crop residue: the photographic and intercept techniques. They are statistical in nature, require multiple assessments, and are also, to some degree, subjective.

The photographic technique consists of taking single down-looking photographs or stereographic pairs of photographs of residue and soil and thereafter manually estimating the fraction of the soil covered by residue from the photographs. Video cameras and computer-aided analysis of the video images of reflected visible light provide enhancements to the photographic technique.

The intercept techniques may be grouped into line-transect and point-intercept methods. With the line-transect method, measurements of crop residue cover are made along the length of a line across the field and average residue cover determined statistically. The point-intercept method uses a system of cross-hairs, grid points, or dot matrices to define points where the presence or absence of residue is determined. At present, the line-transect and point-intercept methods are the most popular methods used to estimate crop residue cover and many variations of these methods have been reported. Sometimes line-transect and point-intercept methods are combined, e.g., a line is placed and the intercept is read at selected points. Accuracy of this line-point transect depends on the length of the line and the number of points used per line.

The disadvantages of the photographic reflected visible light technique are the very slow analysis of the photographs in the laboratory and the special equipment required. Furthermore, there is typically a delay of several days from the date of observation until the analysis is completed. This delay may not be acceptable for making decisions regarding residue management.

Although the line-intercept and point-intercept methods and a combination thereof are deemed to be as accurate as the photographic method, they are slow, tedious, and somewhat subjective. There is a need for a method and apparatus which will overcome these disadvantages. This invention will provide the advantages of rapid, accurate, and objective measurement of crop residue cover to an extent unavailable using current methods and devices, and will provide the added advantage of a readily transportable measurement apparatus.

An additional advantage of this invention is its capability to detect live vegetation, as well as most dead organic matter and to distinguish these from most soils and, further, to measure the rate of decay of the dead organic material covering the soil. The method of this invention will thus be applicable in the field of land assessment, providing a measure of ground cover by organic material and of stress or damage to the vegetative cover.

SUMMARY OF THE INVENTION

Accordingly it is an object of this invention to provide an improved method for discriminating among materials which have different ultraviolet fluorescence signatures.

It is also an object of this invention to provide an improved method for measuring the fraction of the ground at a particular position covered respectively by live vegetation, crop residue (dead organic matter), and soil (composed mostly of inorganic matter).

Another object of the invention is to provide a method for estimating the fraction of an entire field covered respectively by live vegetation, crop residue, and soil.

Still another object of the invention is to provide a method that will give accurate measurements of live vegetation and crop residue cover, of stress or damage to the vegetative cover, and of the rate of decay of dead organic material covering soil.

An additional object of the invention is to provide a method that will offer objective measurements of live vegetation and crop residue cover.

Yet another object of the invention is to provide a method that will offer rapid measurements of live vegetation and crop residue cover.

A further object of the invention is to provide a method for measuring live vegetation and crop residue cover that is capable of distinguishing between live vegetation, dead vegetation, and mineral soil.

A still further object of the invention is to provide a simple ground-based mobile or hand-held apparatus for measuring live vegetation and crop residue cover.

Briefly, in accordance with this invention, these and other objects are attained by providing a method for analyzing the fraction of a surface covered by living plants, dead vegetation, and soil, involving the steps of irradiating the surface with ultraviolet radiation, detecting fluorescent emission emanating from the surface, characterizing a spectral content of the fluorescent emission, and calculating the fraction of the surface covered by the living plants, the dead vegetation, and the soil.

DETAILED DESCRIPTION OF THE INVENTION

Figure 1:
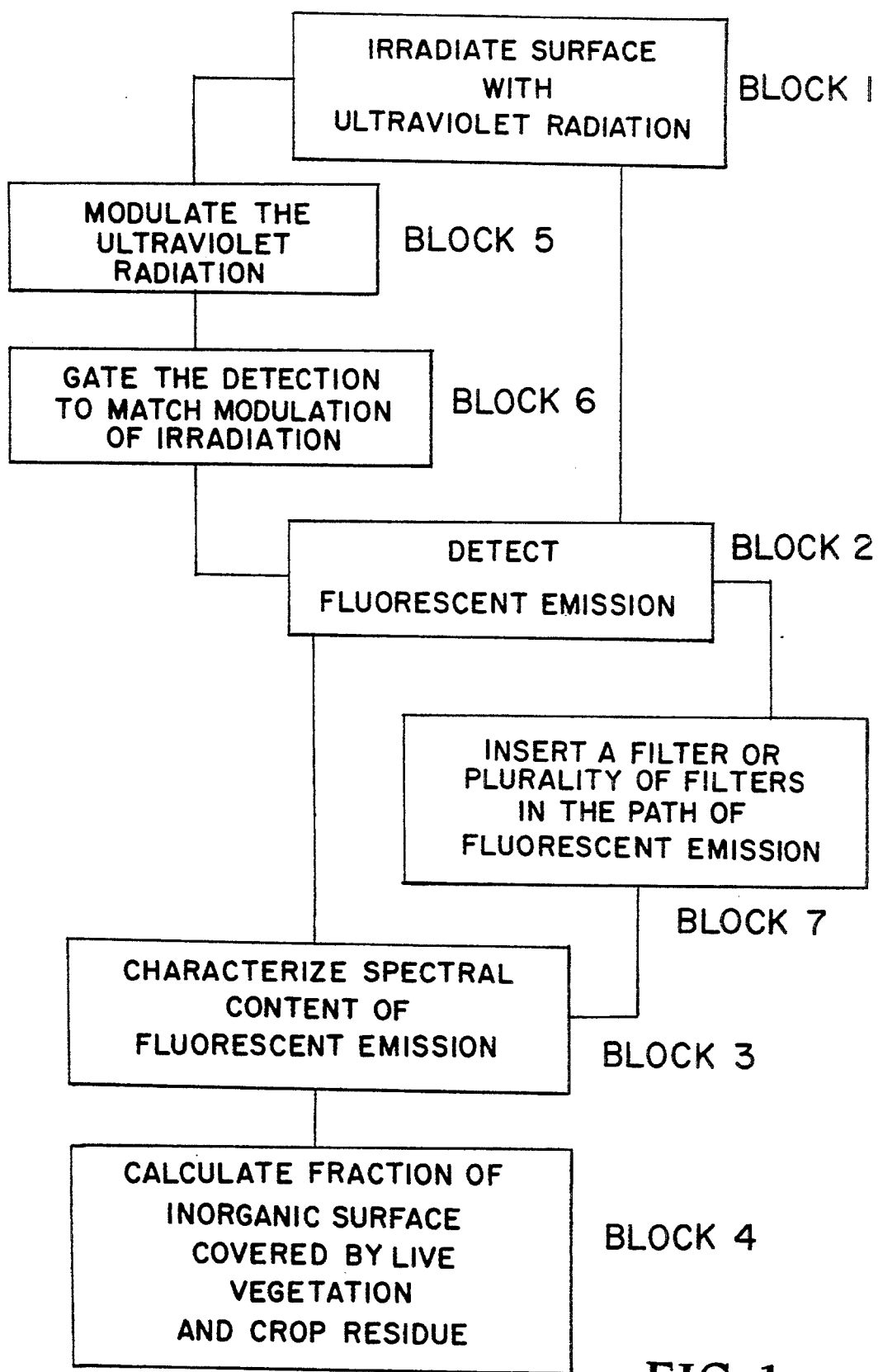
FIG. 1 is a block flow diagram showing the process steps for analyzing the amount of soil surface covered by living plants and dead vegetation.

Referring to FIG. 1 generally, the method for analyzing the fraction of a surface covered respectively by living plants, dead vegetation, and soil is generally shown in Blocks 1 through 4. Block 1 illustrates the step of irradiating the surface with ultraviolet radiation. Block 2 illustrates the step of detecting fluorescent emission from the surface as a result of irradiation. Block 3 illustrates the third step of characterizing the spectral content of the fluorescent emission. Block 4 illustrates the fourth step of calculating from the spectral content of the fluorescent emission the fraction of the surface covered respectively by the live vegetation, the dead vegetation or crop residue, and the soil.

Figure 2:
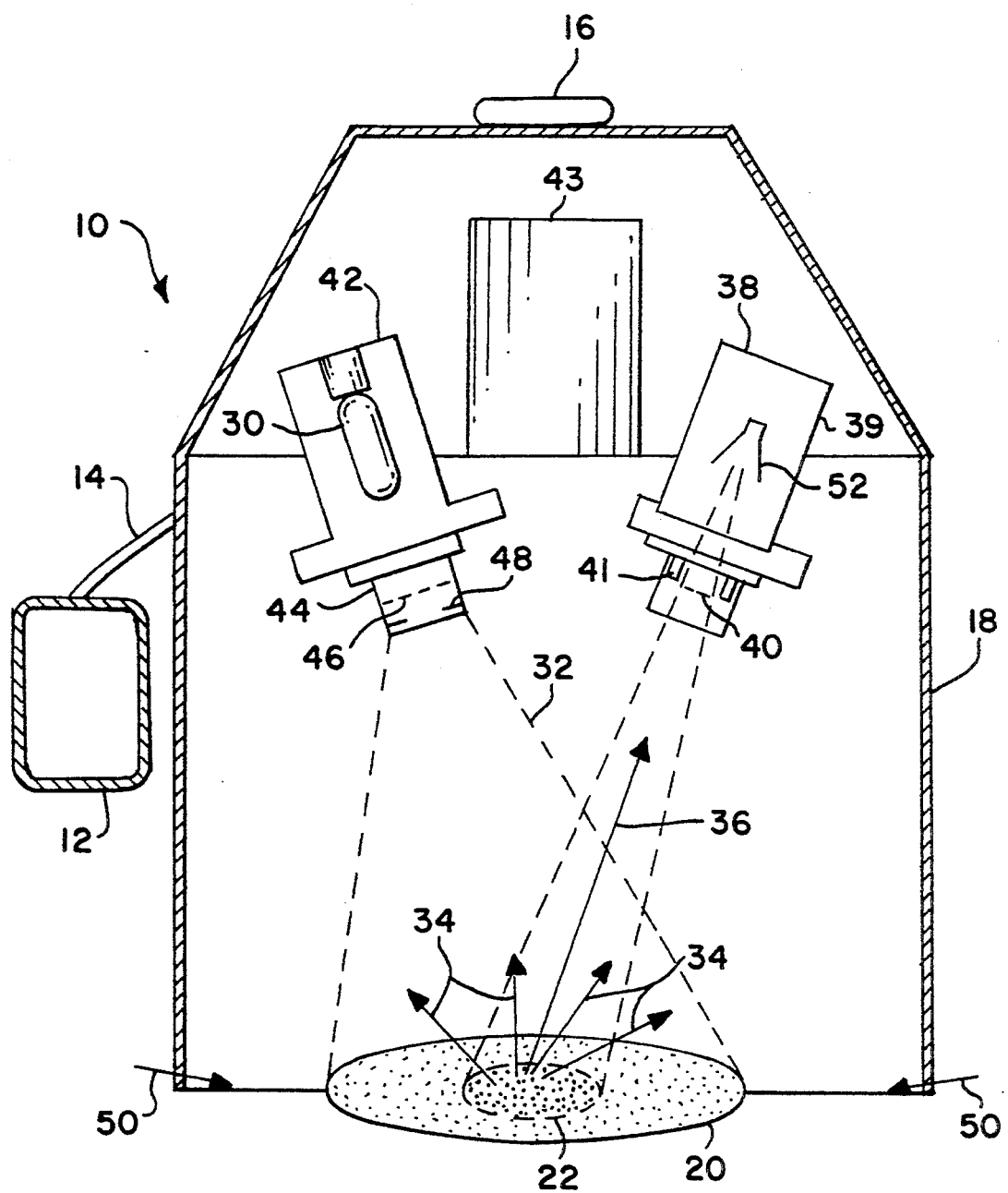
FIG. 2 is an cross-sectional view of the apparatus for performing the process steps of FIG. 1 of the present invention.

More specifically, and again referring to FIG. 1, Block 1 illustrates the first step of illuminating a surface of unknown composition with ultraviolet radiation in the 300–400 nm wavelength range. By virtue of this illumination with ultraviolet radiation, the surface is excited and caused to emit fluorescent radiation if it is comprised of certain molecules. Block 2 illustrates the second step of detecting the quantity of fluorescent radiation emitted by the surface of unknown composition by utilizing a radiation sensor such as shown in FIG. 2 as numeral 52. Block 3 illustrates the third step of characterizing the spectral content of the fluorescent radiation so that, using known spectral characteristics of fluorescent emission by live plants, dead vegetation, and soil, the fractional cover of the surface of unknown composition by each of the respective enumerated constituents can be determined. Block 4 illustrates the forth step of calculating the unknown fractional cover by various constituents from the measured spectral characteristics of the surface and the spectral characteristics of various live and dead vegetation.

Blocks 5 and 6 illustrate the preferred method of performing the first and second steps of Blocks 1 and 2. Illuminating the surface of unknown composition is preferably modulated and the detecting of the emitted fluorescent radiation from the surface is gated to match the modulation of the illumination by the ultraviolet source. Techniques for such modulation are well-known in the art and include flashing the ultraviolet source at periodic intervals and accepting fluorescent signals only for a determined time duration after termination of the flash of the ultraviolet source. Modulating of the source and gating of the detection serve to reject stray signals, to separate ambient light from the fluorescent signal and to improve the accuracy to which a measurement can be made within a determined period of time. Optimized gating should ultimately allow analysis in the presence of stray light and possibly from an aircraft.

Block 7 illustrates that the additional step of characterizing the spectral content of the fluorescent radiation may be accomplished simply by measuring the total amount of fluorescent radiation emitted by the surface and comparing it with known standards. Alternatively, the amount of fluorescent radiation emitted in each of a plurality of spectral bands can be defined by inserting a filter or a plurality of filters in the path between the surface of unknown composition and the sensor, as illustrated in Block 7. By selecting the appropriate wavelength bands and by analyzing the relative spectral contributions of signal in the respective bands, the proportions of the surface of unknown composition covered by live and dead vegetation are determined.

The underlying principle of the method is that when plant material is irradiated with ultraviolet radiation, certain molecules absorb the UV photons and then emit photons of a longer wavelength. The longer-wavelength emission is termed fluorescence and occurs in living plant materials in relatively broad bands with peaks at approximately 440, 525, 685, and 740 nanometers (nm). These bands are in the blue, green, red, and near infrared portions of the spectrum, respectively. By way of example, chlorophyll is responsible for the bands at 685 and 740 nm. Riboflavin is responsible for the band at 525 nm. The bands at 685 and 740 nm progressively disappear as the plant material dies, so that dead vegetation fluoresces primarily from 410 to 550 nm. The compounds that are responsible for intense fluorescence in vegetation in the violet-blue-green region are not found in mineral soil. Therefore fluorescence from 410 to 550 nm can be used to distinguish vegetation from soil. By measuring fluorescence at 685 and 740 nm, one may distinguish between live vegetation and crop residue. The theoretical underpinnings of the method have been reported by the inventors in their papers, "Fluorescence and Reflectance of Crop Residue and Soil," J. Soil & Water Conservation, 48(3), 207–213 (1993), and "Discriminating Crop Residues from Soil by Reflectance and Fluorescence Techniques," IGARSS'93 Digest, 3: 1325–28 (New York: Institute of Electrical and Electronics Engineering, 1993). Both the aforesaid method and the apparatus for carrying out the method as described below have been described in the inventors' article entitled "A Fluorescence Technique for the Assessment of Crop Residue," published in *Research and Technology: 1992 R & T Report*, Greenbelt, MD: NASA Goddard Space Flight Center, (Apr. 20, 1993).

In order to assess fractional surface cover by live vegetation or ground residue, the fluorescent light 34 (in FIG. 2) is quantified. One method which has been demonstrated in the laboratory and has been reported in the inventors' paper, "Fluorescence and Reflectance of Crop Residue and Soil," cited above, entails comparing the fluorescent flux over the entire 415–550 nm wavelength band between bare soil and soil covered with live vegetation or crop residue. Various soils have been characterized by the inventors in the laboratory. The 415–550 nm integrated flux of even the most decomposed crop residue tested was at least double the intensity of the highest integrated flux for the soils tested.

Measuring fluorescent need not be limited to a single band, as in the example described in the preceding paragraph. As testing progresses, a look-up table has been developed on the basis of laboratory results, and increasingly accurate characterization of the fraction of surface covered respectively by live vegetation and crop residue will become possible as the invention is tested and employed in the field. Soils have been tested to form a data base for quantification FIG. 2 generally shows the preferred apparatus for performing the above described method of FIG. 1. Generally, the preferred apparatus, denoted generally by numeral 10, is used for distinguishing various materials 22 which exhibit different fluorescent properties and includes a source 30 of ultraviolet radiation 32 which induces fluorescent emission 34 in the various materials 22. A detecting sensor assembly 38 is coupled to source 30 of ultraviolet radiation 32. A data acquisition system 43 records the quantity of fluorescent emission 34 from the various materials 22 in at least one wavelength band. In this manner, the amount and type of soil cover can be determined by comparison with known spectral characteristics of live and dead vegetation.

Crop residue meter 10 is powered by power source 12 in the form of a 12 or 24 volt battery pack (not shown) or other power sources known in the art. Power source 12 is connected to crop residue meter 10 by an electrical cable 14. In the preferred embodiment, crop residue meter 10 stands about 1.3 meters high and is approximately 30 cm wide, with handles 16 that provide convenient portability. For operation, crop residue meter 10 is placed over the sample surface 20. Crop residue meter 10 is preferably enclosed within a light tight hood 18. Light tight hood 18 encloses excitation source 30 and sensor assembly 38, and positions both excitation source 30 and sensor assembly 38 at a fixed distance, preferably approximately 1 meter, above sample surface 20. Excitation source 30 is preferably an ultraviolet lamp such as a xenon lamp that is approximately 1 inch in diameter and which emits light in the 300–400 nm wavelength range. Although excitation source 30 is preferably an ultraviolet excitation lamp, other excitation sources 30 may be used, and it may be a monochromatic source of radiation, such as a laser emitting radiation at a wavelength shortward of 370 nm. Excitation source 30 is encased in a source assembly 42 that is about 3 cm in diameter and which serves to prevent stray radiation from reaching sensor assembly 38, and is covered by a filter holder 44 which contains a 300–390 nm cut off filter 46. Cut off filter 46 prevents injection into sensor assembly 38 of light from excitation source 30 at wavelengths longer than 370 nm which is not due to fluorescence.

Modulation of excitation source 30 is accomplished, in the preferred embodiment, by means of an electromechanical shutter 48 to further ensure that any light sensed by sensor assembly 38 is due to, and thus contemporaneous with, illumination by excitation source 30 and not due to ambient light 50 which leaks in through light tight hood 18. Other means of modulating excitation source 30 would include the use of an electro-optical shutter (not shown) or electrical modulation of the emission of source 30 itself such as by pulsing its electrical power.

Detection of fluorescent light 34 emitted along path 36 toward sensor assembly 38 is accomplished by means of sensor 52 enclosed within sensor assembly 38. Sensor 52 is preferably a photomultiplier tube, but can be any of several means of detecting ultraviolet radiation which are well-known in the art. Sensor assembly 38 is encased in a tube 39 that is approximately 3 centimeters in diameter. Sensor assembly 38 further contains a filter assembly 40 which contains a plurality of filters 41 which can be inserted sequentially between sample surface 20 and sensor 52 in order to limit fluorescent light 34 which reaches sensor 52 to a specific band of wavelengths. Electronic signals from sensor assembly 38 are processed by data acquisition system 43, which digitizes, records, and analyzes measurements of fluorescent light 34.

Figure 3:
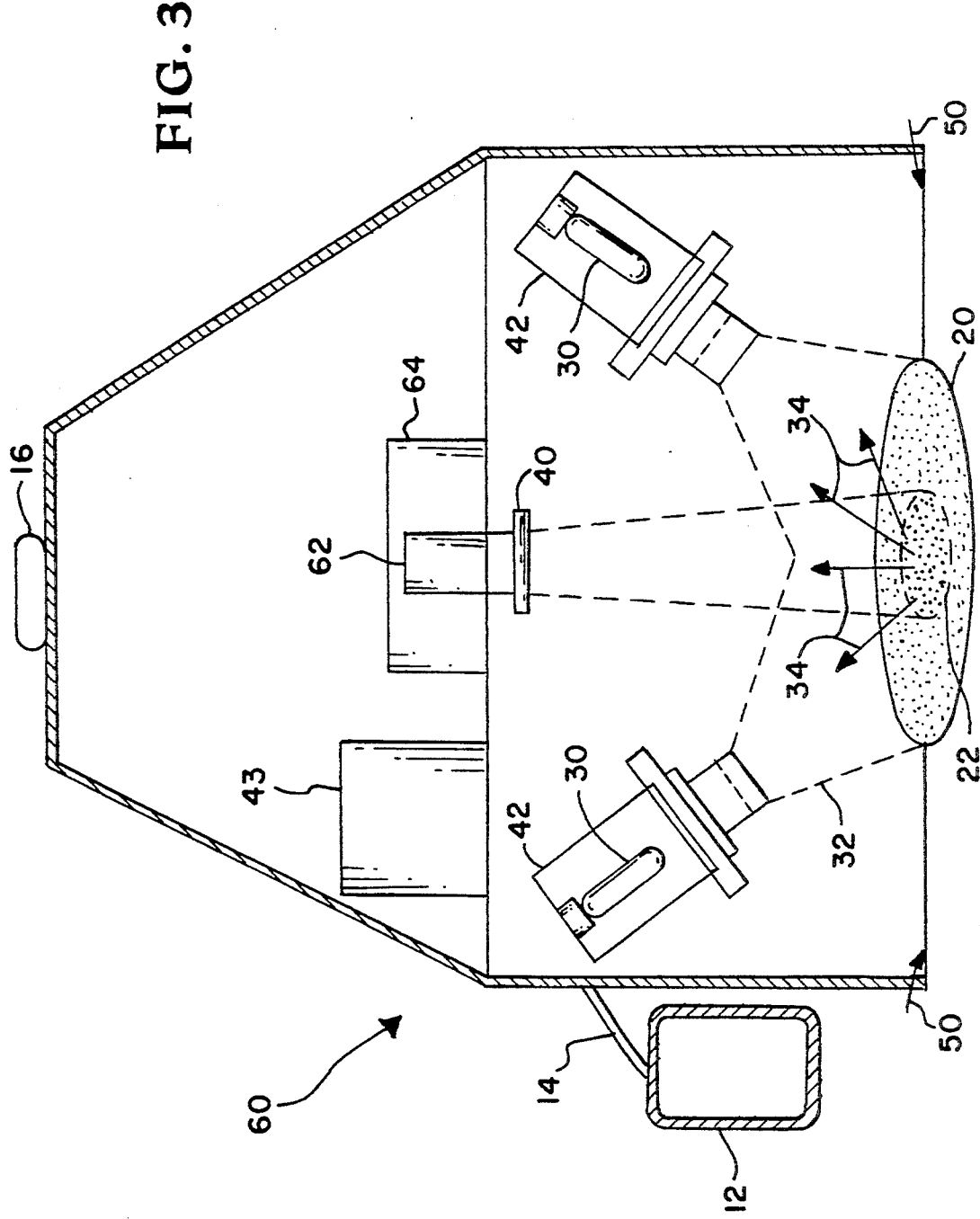
FIG. 3 is a cross-sectional view of the apparatus for performing the process steps of FIG. 1 of the present invention showing the imaging capability of the apparatus.

Referring now to FIG. 3, which depicts an alternative embodiment of this invention designated generally by numeral 60, alternative embodiment 60 similarly contains source assembly 42 which provides for ultraviolet irradiation of sample surface 20. Light-tight hood 18 additionally encompasses sensory assembly 62 which, in this embodiment, contains a video camera 64 comprised of multiple pixels which are sensitive to the fluorescent light 34 emitted by sample surface 20. Alternative embodiment 60 operates in the same manner as crop residue meter 10 depicted in FIG. 1, with the additional capacity of characterizing multiple areal elements of sample surface 20.

Figure 4:
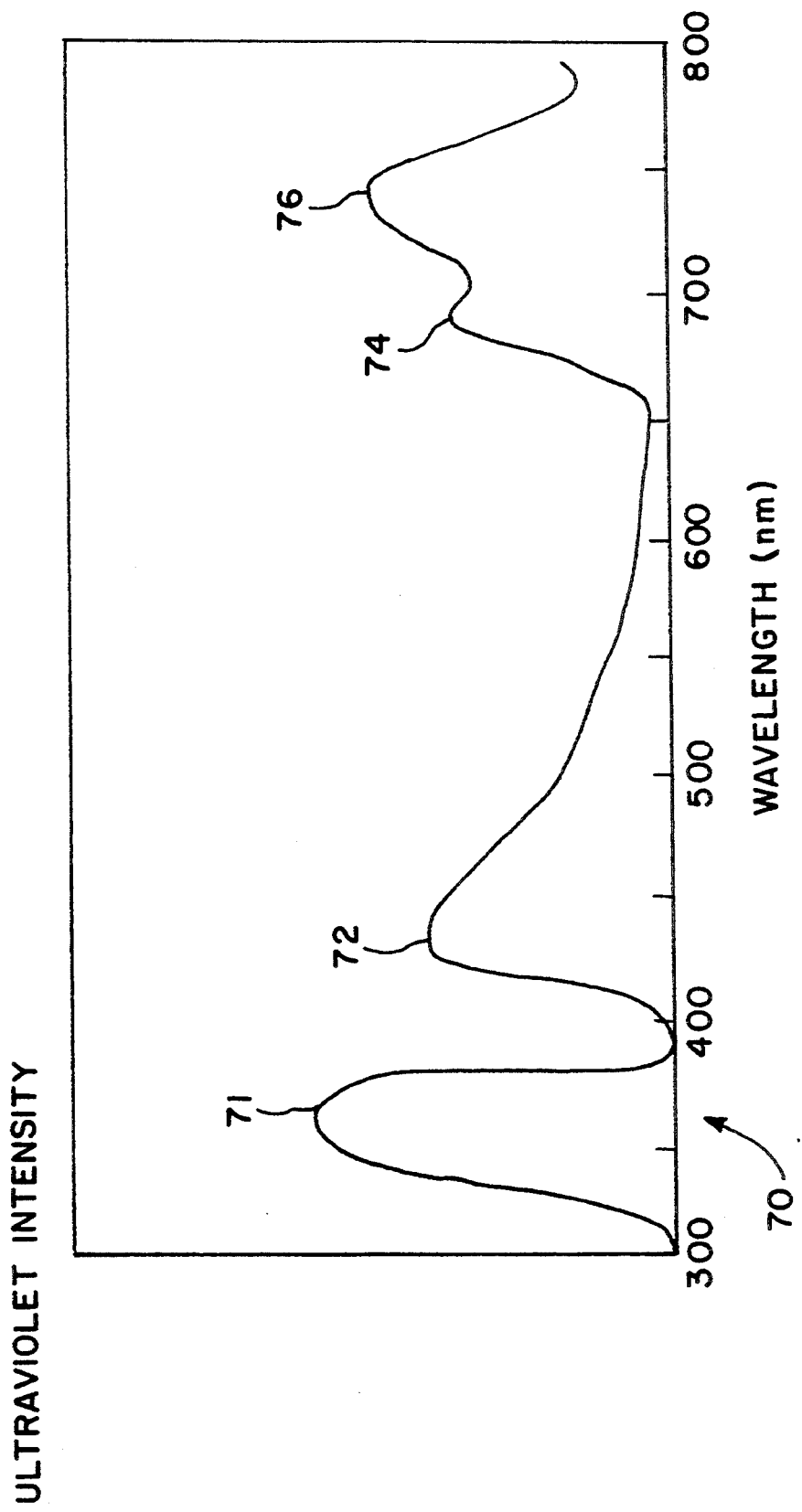
FIG. 4 is a depiction of the spectrum of fluorescent light emitted by the illuminated sample.

In operation, the preferred crop residue meter, designated generally by numeral 10 (in FIG. 2) is placed over a sample surface 20, which may be the ground when the crop residue meter 10 is being used to measure the fraction of ground surface covered by crop residue 22. Excitation source 30 emits a beam of exciting ultraviolet radiation 32 which is used to illuminate sample surface 20. Fluorescent light 34 is emitted by sample surface 20 in all directions. The spectrum of wavelengths generally shown as numeral 70 in FIG. 4, which comprises fluorescent light 34, is characteristic of the composition of sample surface 20. Exciting ultraviolet excitation illumination 32 is characterized by a wavelength 71 shortward of 390 nm. A portion of fluorescent light 34 is emitted along path 36 toward sensor assembly 38. Wavelength components 72, 74, 76 of fluorescent light 34 are detected separately by sensor assembly 38. In the preferred embodiment illustrated in FIG. 2, this is accomplished by means of serially inserting a plurality of spectral filters 40 into path 36 between sample surface 20 and sensor assembly 38. The relative quantities of fluorescent light 34 registered at sensor assembly 38 through each of plurality of spectral filters 40 is electronically logged by data acquisition system 43. Data acquisition system 43 applies a computational algorithm, known to the art of spectroscopy, in order to derive the fluorescent spectrum of wavelengths 70 (shown in FIG. 4) of sample surface 20 and to infer the fraction of sample surface 20 covered by crop residue 22. Now referring back to FIG. 2, the electrical signal from sensor assembly 38 is digitized, processed, recorded, and analyzed electronically by data acquisition system 43.

The operation of crop residue meter 10 is more particularly described as follows: first, crop residue meter 10 is zeroed. This process involves making sure the readouts are at zero when the system is in the dark. A reading is also taken on a plot of bare mineral soil, this provides a baseline reading for the area to be surveyed. Next the user transports crop residue meter 10 along a preselected path (not shown) and places it on surface 20 that is to be surveyed at calculated intervals. At each position, excitation source 30 is turned on in a modulated manner. By limiting the detection to a signal which is synchronous with the modulation of excitation source 30, an increase in signal-to-noise is achieved, and the efficiency of the soil assessment process is thereby enhanced. The temporal window following emission of the exciting radiation 32 to which signal detection is limited may be varied to achieve optimum signal-to-noise. Data acquisition system 43, which may be an electronic computer, records the relative fluorescent intensity at each of the locations at which measurements are made, and calculates the proportion of the area sampled (not shown) covered by residue or vegetation 22.

The method taught in the aforesaid description thus provides for discriminating among materials which have different ultraviolet fluorescent signatures. In particular, live vegetation and crop residue may be discriminated from bare soil and also from each other. The method may be applied in sampling the ground cover of an entire field. The method described is rapid in that the device is hand-held and readily portable, being battery powered and self-contained. The measurement of ground cover provided by the invention is objective in that the algorithm resident in the electronic computer (not shown) is applied to each sample surface 20 without subjective evaluation, and is thus an accurate measurement.

While the specific method and disclosed relates the analysis of soil and vegetation at a particular location, the method is generally applicable to discriminating between differing materials that, when excited by a given radiation source, fluoresce at differing wavelengths. Obviously, many modifications and variations of the present invention are possible in light of the above teachings. It is therefore to be understood that within the scope of the appended claims the invention may be practiced otherwise than as specifically described.

We claim:

1. A method for analyzing the fraction of a surface covered respectively by living matter, dead organic matter, and nonorganic matter, comprising the steps of:
   (a) irradiating said surface with ultraviolet radiation to produce fluorescence;
   (b) detecting an emitted fluorescent emission emanating from said surface;
   (c) characterizing a spectral content of said emitted fluorescent emission; and
   (d) calculating the fraction of said surface covered respectively by said living matter, said dead vegetation, and said nonorganic matter.

2. The method as defined by claim 1, wherein said method further includes:
   modulating said ultraviolet radiation; and
   detecting said emitted fluorescent emission emanating from said surface by means of a gated detection device.

3. The method as defined by claim 1, wherein said step of (c) includes passing said emitted fluorescent emission though at least one spectral filter.

4. The method as defined by claim 1, wherein said step of (c) includes passing said emitted fluorescent emission though a plurality of spectral filters.

5. The method as defined by claim 1, in which steps (a) through (c) are applied at a plurality of positions.

6. The method as defined by claim 5, in which a statistical estimate is performed as to the properties of the ensemble of positions.

* * * * *